US005212321A

United States Patent [19]

Muller et al.

[11] Patent Number: 5,212,321

[45] Date of Patent: May 18, 1993

[54] PROCESS FOR THE PREPARATION OF TRIMETHYLENE CARBONATE

[75] Inventors: Klaus R. Muller; Berthold Buchholz, both of Ingelheim am Rhein; Joachim Hess, Bingen, all of Fed. Rep. of Germany

[73] Assignee: Boehringer Ingelheim GmbH, Ingelheim am Rhein, Fed. Rep. of Germany

[21] Appl. No.: 900,519

[22] Filed: Jun. 17, 1992

Related U.S. Application Data

[63] Continuation of Ser. No. 582,561, Sep. 14, 1990, abandoned.

[30] Foreign Application Priority Data

Oct. 7, 1989 [DE] Fed. Rep. of Germany ....... 3933617

[51] Int. Cl.[5] .................... C07D 317/38; C07D 319/06

[52] U.S. Cl. ..................................... 549/228; 549/230

[58] Field of Search ................................ 549/228, 230

[56] References Cited

U.S. PATENT DOCUMENTS

| | | | |
|---|---|---|---|
| 4,786,741 | 11/1988 | Sachs | 549/230 |
| 5,091,543 | 2/1992 | Grey | 549/230 |
| 5,118,818 | 6/1992 | Delledonne et al. | 549/228 |

FOREIGN PATENT DOCUMENTS

| | | |
|---|---|---|
| 0293690 | 12/1988 | European Pat. Off. . |
| 0300794 | 1/1989 | European Pat. Off. . |
| 2286987 | 12/1987 | Japan . |

*Primary Examiner*—C. Warren Ivy
*Assistant Examiner*—A. A. Owens
*Attorney, Agent, or Firm*—David E. Frankhouser; Alan R. Stempel; Mary-Ellen M. Timbers

[57] ABSTRACT

A process for producing trimethylene carbonate wherein 1,3-propanediol is reacted with diethylcarbonate in the presence of zinc powder, zinc oxide, tin powder, tin halide or an organo-tin compound, at an elevated temperature.

10 Claims, No Drawings

PROCESS FOR THE PREPARATION OF TRIMETHYLENE CARBONATE

This is a continuation of application Ser. No. 582,561, filed Sep. 14, 1990 now abandoned.

The present invention relates to a new, industrially applicable process for preparing cyclic carbonic acid esters of general formula I

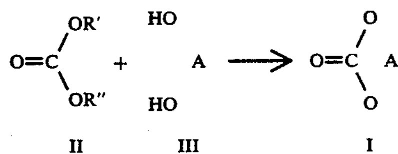

wherein

A represents an optionally substituted alkylene bridge of the following type $-CR^1R^2-CH_2-$, $-CHR^1-CHR^2-$, $-CR^1R^2-(CH_2)_2-$, $-CHR^1-CHR^2-CH_2-$, $-CH_2-CR^1R^2-CH_2-$, $-CHR^1-CH_2-CHR^2-$, and $R^1$ and $R^2$ may be identical or different and may denote hydrogen, methyl, ethyl, propyl, isopropyl, n-butyl, sec-butyl, tert.butyl, allyl, but-2-enyl, .but-3-enyl, pent-2-enyl, pent-3-enyl, pent-4-enyl, phenyl or benzyl and R and R" may denote methyl, ethyl, propyl or phenyl.

Cyclic carbonic acid esters are used on the one hand as solvents, such as ethlenecarbonate (1,3-dioxolan-2-one), and on the other hand they are essential building blocks of so called bio-degradable polymers, such as trimethylenecarbonate (1,3-dioxan-2-one) which may in turn be used in a variety of applications (surgical stitching material, vessel implants, apparatus for osteo-synthesis).

The use of solvents, and also to a particular degree, the use in the synthesis of biodegradable polymers, make major demands on the purity of the carbonic acid esters in question.

Thus, when they are used as solvents, there is a danger that the impurities in the solvent will accumulate in the originally dissolved substance when the solvent is eliminated.

On the other hand, the physical and chemical properties of the above mentioned polymers, such as their tensile strength, the molecular mass achievable on polymerisation and the rate of degradation (rate of hydrolysis) are particularly liable to be influenced by the purity of the monomers used e.g. trimethylenecarbonate.

Moreover, from the point of view of industrial production of the cyclic carbonic acid esters, it is desirable to find a method of synthesis yielding cyclic carbonates which satisfy all the purity criteria if possible, and at the same time can be produced in high yields, by the simplest possible industrial process.

Numerous methods are known for producing carbonic acid esters [Ullmann's Encyclopaedia of Industrial Chemistry, Volume 5, Fifth edition, VCH Verlagsgesellschaft, Weinheim 1986, Page 197 ff and literature cited therein, Kirk-Othmer, Encyclopaedia of Chemical Technology, Volume 5, John Wiley and Sons, New York N.Y. 1978, Page 766 ff and literature cited therein], of which only the reactions of phosgene with alcohols or the base-catalysed transesterfications of suitable carbonic acid esters, will be mentioned by way of example at this point.

In addition, the trans-esterfications of diethylcarbonate with propane-1,3-diol in the presence of sodium or sodium methoxide to obtain trimethylenecarbonate is one of the oldest methods of production [W. H. Carothers and F. V. Natta, J Am. Chem. Soc. 52 (1930) 322; S. S. Sarel, L. A. Pohoryles and R. Ben-Shoshan, J. Org. Chem. 24 (1959) 1873], but the purity of the product obtained is nowhere near sufficient in view of its use in polymerisation reactions and results in a lower grade product. In addition, the unsatisfactory yield makes this reaction unsuitable for industrial use.

The aim of the present invention is to provide a process which enables carbonic acid esters to be produced in an industrially applicable manner and in good yields.

A further aim of the invention is to provide a process for preparing cyclic carbonic acid esters-particularly of 1,3-dioxan-2-one (trimethylenecarbonate) yielding a carbonic acid ester which has a purity sufficient to allow the cyclic carbonate to be used in the production of high molecular weight polyesters.

According to the invention, the problem is solved by reacting an open-chained dialkylcarbonate of general formula II, wherein R' and R" independently of each other may represent methyl, ethyl, propyl or phenyl-preferably diethylcarbonate-with a diol of general formula III wherein A is defined as herein before, preferably with 1,3-propanediol — in the presence of zinc powder, zinc oxide, tin powder, a tin halide such $SnCl_2$ or $SnBr_2$ — or an organo-tin compound at elevated temperature in the range from 120°-180° C. preferably in the range from 140°-150° C. Depending on the reactivity of the carbonic acid ester and the catalyst, it may also be necessary to select a higher or lower reaction temperature. The catalysts used may be, other than the above mentioned elements or compounds, tin compounds of

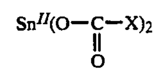

wherein X represents a branched or unbranched alkyl, or hydroxyalkyl or alkenyl group having up to 19 carbon atoms, or a methyl group, or compounds of general structure

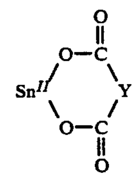

wherein Y represents a branched or unbranched alkylene, hydroxyalkylene or alkenylene group with up to 18 carbon atoms or a phenyl group.

Suitable alkyl or alkylene groups for X and Y include, e.g. methyl, ethyl, n-or iso-propyl, n-, sec.- or tert. butyl, pentyl-, hexyl-, heptyl, which may optionally contain one or more hydroxy groups. Corresponding alkenyl or alkenylene groups contain 1 or more double bonds.

Preferred catalysts are tin lactate, tin tartrate, tin oxalate, tin dicaprylate, tin dilaurate, tin dipalmitate, tin distearate, tin dioleate (derivative of oleic acid) tin-α-napthoate and tin-β-dioctoate - also known as tin-di(2-ethylhexanoate) - or tin or zinc powder of which tin and zinc powder and tin-di(2-ethylhexanoate) are particularly preferred.

Subsequently, the volatile by-products and unreacted educts are distilled off at elevated temperature, in a temperature range from 80° C. to 150° C. and preferably in the range from 80° to 130° C. and optionally under reduced pressure.

Again, it may be necessary to select a higher or lower temperature or to choose a lower pressure depending on the educts or the by-products.

The distillation residue is then distilled by fractional distillation under reduced pressure — preferably in a high vacuum — and re-crystallised if necessary. The examples which follow are intended to illustrate the invention without restricting it.

EXAMPLE 1

761 g of 1,3-propanediol, 1477 g of diethycarbonate and 50 g of tin powder are added successively to a 2.5 liter sulphating flask. At an oil bath temperature of 150° C. distillation is then carried out using dephlegmator (80° C.). After distillation has ended the dephlegmator is removed, the bath temperature is lowered to 130° C. and distillation is continued under a slight vacuum. The viscous distillate is transferred into a 2 liter flask and fractionated under a high vacuum (bath temperature up to 180° C.). A main-fraction of 923 g (=90% of theory) is obtained. Recrystallisation of this fraction from acetone/diethylether yields 803 g (=79% of theory) of purified product.

POLYMERISATION EXAMPLE 3.0 g of the trimethylenecarbonate obtained and purified in Example 1, are polymerised at 190° C. in a glass test-tube fused under nitrogen, with the addition of 1-dodecanol and $SnCl_2$ x2 $H_2O$. The conversion of trimethylenecarbonate is 97% ($^1H$-NMR, $CDCl_3$, 250 MHz).

The inherent viscosity of the polymer (measured in 0.1% solution in $CHCl_3$ at 25° C.) is 1.22 dl/g.

EXAMPLE 2

380.5 g of 1,3-propandiol, 649.7 g of diethylcarbonate and 30 g of zinc powder are placed in a 1.5 liter sulphating flask. At a bath temperature of 140°-175° C. the ethanol formed during the reaction is distilled off through a charged column whilst the reaction mixture is stirred thoroughly.

After the reaction has ended, the reaction mixture obtained is fractionally distilled in vacuo. (0.3-0.5 mbar). A main fraction of 450 g is obtained which is precipitated as a melt in methyl-tert.butylether. After suction filtering, the product is dried at 20° C. in a vacuum drying cupboard.

Yield: 401.7 g=78.7% of theory.

The polytrimethylene carbonate prepared from this product (c.f. the polymerisation example given above) has an inherent viscosity of 1.5 dl/g (measured in 0.1% solution in $CHCl_3$ at 25° C.).

EXAMPLE 3

401.7 g of the trimethylenecarbonate obtained in Example 2 are melted and precipitated in petrol (fraction 40°-60° C.). After isolation and drying, the inherent viscosity of the polymer produced therefrom (see polymerisation Example) is 1.75 dl/g.

Yield: 395.7 g=98% of theory.

EXAMPLE 4

401.7 g of the trimethylenecarbonate obtained Example 2, are re-crystallised from dried toluene. After isolation and drying, polytrimethylenecarbonate prepared therefrom (See polymerisation Example), has an inherent viscosity of 1.98 dl/g.

Yield: 364.3 g=90.7% of theory.

What is claimed is:

1. A process for producing trimethylene carbonate wherein 1,3-propanediol is reacted with diethylcarbonate in the presence of zinc powder, zinc oxide, tin powder, tin halide or an organo-tin compound, at an elevated temperature.

2. A process for producing trimethylene carbonate wherein 1,3-propanediol is reated with diethylcarbonate in the presence of zinc powder, at a temperature between about 120° and 180° C.

3. The process according to claim 1, further characterised in that zinc powder, zinc oxide, tin powder or a tin halide is used as catalyst.

4. The process according to claim 1, further characterised in that the catalyst used is a compound of the formula

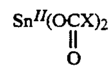

wherein

X denotes a branched or unbranched alkyl, hydroxy alkyl, or alkenyl group with up to 19 carbon atoms, or a napthyl group or a compound of the formula

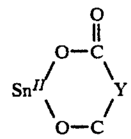

wherein

Y may represent a branched or unbranched alkylene, hydroxyalkylene or alkenylene group with up to 18 carbon atoms, or a phenyl group.

5. The process according to claim 1, further characterised in that an organo-tin compound is used as catalyst.

6. The process according to claims 1, 2, 3, or 4, further characterised in that the reaction temperature is in the range from 120°-180° C.

7. The process according to claims 1, 2, 3 or 4, further characterised in that the reaction temperature is in the range from 140°-150° C.

8. The process according to claim 1, further characterised in that zinc powder is used as catalyst.

9. The process according to claim 1, further characterised in that, after the reaction has ended, volatile reaction products are eliminated from the reaction mixture by distillation.

10. The process according to claim 1, further characterised in that the resulting cyclic carbonic acid ester is purified by fractional distillation.

* * * * *